US006393906B1

(12) United States Patent
Vityk et al.

(10) Patent No.: US 6,393,906 B1
(45) Date of Patent: May 28, 2002

(54) METHOD TO EVALUATE THE HYDROCARBON POTENTIAL OF SEDIMENTARY BASINS FROM FLUID INCLUSIONS

(75) Inventors: Maxim O. Vityk, Pearland; Robert H. Pottorf, Houston, both of TX (US); Robert J. Chimenti, Short Hills; Patricia H. Kalamaras, Milford, both of NJ (US); Robert J. Bodnar; Jing Leng, both of Blacksburg, VA (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 09/870,320

(22) Filed: May 30, 2001

Related U.S. Application Data
(60) Provisional application No. 60/265,654, filed on Jan. 31, 2001.

(51) Int. Cl.[7] .......................... E21B 47/06; E21B 43/16
(52) U.S. Cl. ..................... 73/152.51; 166/269
(58) Field of Search .................. 73/152.51, 152.44, 73/152.52; 702/9; 166/269, 223, 268

(56) References Cited

PUBLICATIONS

Dubessy, J. et al, "Methane–Bearing Aqueous Fluid Inclusions: Raman Analysis, Thermodynamic Modelling and Application To Petroleum Basins", Chemical Geology, vol. 173, published on Mar. 1, 2001, pp. 193–205. (Accepted on Jan. 18, 2000, as outlined in the J. Leng abstract listed below).
Dubessy, J. et al, "Analysis of Methane At Low Concentration In Fluid Inclusions With Raman Spectroscopy", PACROFI 1998, Las Vegas, Nevada.
Leng, J. et al, "Quantitative Analysis of Synthetic Fluid Inclusions In the $H_2O–CH_4$ System Using Raman Spectroscopy", PACROFI 1998, Las Vegas, Nevada.
Seitz, J. C., et al., "Raman Spectroscopic Characterization of Gas Mixtures II. Quantitative Composition and Pressure Determination of the CO2–CH4 System", American Journal of Sciences, 296, 1996, pp. 577–600.
Pironon, J. et al., "Volumetric Reconstruction of Individual Oil Inclusions by Confocal Scanning Laser Microscopy", Eur. J. Mineral, 10 1998, pp. 1143–1150.
Aplin, A. C., et al., "Combined Use of Confocal Laser Scanning Microscopy and PCT Simulation for Estimating the Composition and Physical Properties of Petroleum in Fluid Inclusions", Mar. Petroleum Geology, 16, 1999, pp. 97–100.
Aplin, A. C., et al., "Confocal Microscopy of Fluid Inclusions Reveals Fluid Pressure Histories of Sediments and an Unexpected Origin of Gas Condensate", Geology, No. 11, 2000, pp. 1047–1050.
Roeder, E. and Bodnar, R. J., "Geologic Pressure Determination From Fluid Inclusion Studies", Ann. Rev. Earth. Planet. Sci. 8, 1980, pp. 263–301.
Mernagh, T. P. and Wilde, A. R., Geochimica et Cosmochimica Acta, 53, 1989, pp. 765–771.

*Primary Examiner*—Hezron Williams
*Assistant Examiner*—Jay Politzer
(74) *Attorney, Agent, or Firm*—Gary P. Katz (57) ABSTRACT

A method for evaluating sedimentary basins for hydrocarbon potential using aqueous fluid inclusions. Aqueous fluid inclusions are identified in a rock sample. The homogenization temperatures of the fluid inclusions are determined, the optical spectra of the water and methane in the fluid inclusions are measured, and the formation pressures are estimated from the relationship of homogenization temperature and optical spectrum to formation pressure. Formation pressure of the fluid inclusions can be combined with history of the fluid inclusion formation to reconstruct the paleohistory of the basin to evaluate hydrocarbon potential.

30 Claims, 5 Drawing Sheets

METHOD TO EVALUATE THE HYDROCARBON POTENTIAL OF SEDIMENTARY BASINS FROM FLUID INCLUSIONS

This application claims the benefit of U.S. Provisional Application No. 60/265,654 filed on Jan. 31, 2001.

FIELD OF THE INVENTION

This invention relates generally to the field of oil and gas exploration. More particularly, this invention relates to the use of aqueous and oil inclusions in rocks to reconstruct paleo-pressure history to evaluate hydrocarbon potential of sedimentary basins.

BACKGROUND OF THE INVENTION

A critical component of petroleum exploration involves characterizing the risk associated with the timing of hydrocarbon migration and trap fill, reservoir pressure history, and timing of seal failure. This requires reliable estimates of paleo-pressure. Paleo-pressure is the ancient pressure of the sedimentary basin (i.e., the pressure during formation of the sedimentary basin). Paleo-pressure estimation has proven to be difficult to quantify and there is a need for an accurate and low-cost method of measuring paleopressure directly from geological samples.

The only known technique for directly measuring geological paleopressure utilizes fluid inclusions in rocks. Fluid inclusions are microscopic samples of paleo-fluids that are trapped and sealed within cavities in minerals. These inclusions preserve the pressure at which they were trapped. Several methods have been used to obtain trapping pressure from fluid inclusions in petroleum systems. For example, pressure from individual methane-carbon dioxide ($CH_4$—$CO_2$) gas inclusions can be obtained by using Raman spectral parameters (Seitz, J. C., Pasteris, J. D., and Chou I-M., 1996. Raman spectroscopic characterization of gas mixtures. II. Quantitative composition and pressure determination of the $CO_2$—$CH_4$ system. American Journal of Sciences, 296, 577–600). The underlying principle of Raman spectral analysis is when monochromatic (i.e. substantially single photon energy) light, such as emitted from a laser traverses a medium (e.g. gas, liquid, or solid) the majority of the scattered light will remain at the incident photon energy. However, a small proportion of the scattered light will be at changed frequencies, above and below the incident photon energy, and this is referred to as anti-Stokes and Stokes Raman scattering, respectively. The energy increment and decrement for the anti-Stokes and Stokes scattering, respectively correspond to the vibrations of the molecules of the medium that produce the scattered photons.

By measuring the energy decrement of the scattered light relative to the incident light, Raman spectroscopy is a tool to probe molecular vibrations. As Raman spectroscopy may be carried out within the ultra-violet (UV) and visible regions of the spectrum, the incident laser beam can be focused by normal light optics, i.e. microscope objectives, to give spatial resolution in the region of 1 micrometer. It therefore provides a non-destructive means of analyzing the molecular species of very small objects, including fluid inclusions in minerals. This technique has proven to be particularly successful for the analysis of species such as carbon dioxide ($CO_2$), carbon monoxide (CO), methane ($CH_4$), ethane ($C_2H_6$), nitrogen ($N_2$), water ($H_2O$), hydrogen sulfide ($H_2S$), hydrogen sulfite ($H_2SO_3$), oxygen ($O_2$), and sulfates ($SO_4^{-2}$).

Laser photon energies in the range of 50000 $cm^{-1}$ to 9000 $cm^{-1}$ may be used for excitation. The Raman scattered radiation is detected over a range of 150 $cm^{-1}$ to 4600 $cm^{-1}$ below the laser excitation energy. Preferably, the inclusion to be analyzed is illuminated through a microscope and a portion of the backscattered laser excitation and Raman emission are collected and collimated by the objective. Other angles between incident and scattered laser light may be used. Filters separate the laser and Raman components and the latter is recorded by a spectrometer.

Inclusion trapping pressure from Seitz et al. method can be obtained from the peak positions of the $CH_4$ and $CO_2$ Raman bands obtained from gas inclusions. However, this application is limited to pure $CH_4$, $CO_2$ and/or $CH_4$—$CO_2$-bearing inclusions, which are rare for petroleum systems. Raman spectroscopy was also used to obtain minimum trapping pressure from synthetic $CH_4$-bearing aqueous fluid inclusions (Dubessy, J., Pironon, J., Lamb, W., McShane, C., Popp, C., Thiery, R., 1998. PACROFI VII, Jun. 1–4, 1998, 27, Leng, J., Sharma, A., Bodnar, R. J., Pottorf, R. J., Vityk, M. O., 1998. Quantitative Analysis of Synthetic Fluid Inclusions in the $H_2O$—$CH_4$ System Using Raman Spectroscopy. PACROFI VII, Jun. 1–4, 1998, 41).

The method of Dubessy et al. uses microthermometry to determine the salinity of the aqueous phase, and Raman spectra of methane and water and the thermodynamic properties of the water-methane ($H_2O$—$CH_4$), no salt, system to model the inclusion methane content. Microthermometry is the observation of the temperatures of phase changes within fluid inclusions as they are cooled or heated on a special microscope stage. This method can provide two basic kinds of information: inclusion composition and temperature of entrapment. The temperature of ice melting tells us something about chemistry of inclusion fluid and the temperature of the inclusion bubble (gas phase) disappearance (homogenization temperature) is a minimum or true value for the temperature at which the inclusion was trapped. The inclusion composition and homogenization temperatures are used to obtain the pressure at the bubble point. Bubble point pressure is the pressure at inclusion saturation or saturation pressure. However, the Dubessy et al. method has a number of limitations.

One of these limitations is that this method can not be used to obtain the true trapping pressure. Reliable pressure measurements from fluid inclusions are entirely dependent on the specific type of fluid inclusions measured. Some fluid inclusions can be used to determine only a minimum pressure of entrapment, some may be used to determine the true pressure of entrapment. Fluid inclusions that can be used to determine the true pressure of entrapment need to be recognized in the rock based on a unique set of petrographic and microthermometric criteria. The Dubessy et al. method provides no such criteria.

Additional limitations of the Dubessy et al. method include 1) lack of calibration with application to natural petroleum systems of interest which contain salt and generally homogenize at temperatures below 300° C., and 2) the necessity for additional calibration for the effect of salinity. Application of the method to determine the potential for hydrocarbons is not discussed.

The work of Leng et al. reports the Raman band area ratio for synthetic $CH_4$- water (no salt) inclusions and discusses neither the determination of the formation pressure from the Raman data nor the use of the pressure determination for hydrocarbon exploration applications.

The bubble point pressure or saturation pressure can be obtained from individual oil inclusions by using confocal scanning laser microscopy coupled with microthermometry (Pironon, J., Canals, M., Dubessy, J., Walgenwitz, F., Laplace-Builhe, C., 1998. Volumetric Reconstruction of Individual Fluid Inclusions By Confocal Scanning Laser Microscopy. Eur. J. Mineral. 10, 1143–1150, Aplin, A. C., Macleod, G., Larter, S. R., Sorensen, H., Booth, T, 1999. Combined Use of Confocal Laser Scanning Microscopy and PVT Simulation For Estimating the Composition and Physical Properties of Petroleum in Fluid Inclusions. Mar. Petrol. Geol. 16, 97–100, Aplin, A. C., Larter, S. R., Bigge, M. A., Macleod, G., Swabrick, R. E., Grunberger, D., 2000, Confocal microscopy of fluid inclusions reveals fluid pressure histories of sediments and an unexpected origin of gas condensate. Geology, no. 11, 1047–1050). This method involves generation of three-dimensional images of an individual oil inclusion by using confocal scanning laser microscopy and calculation of the volumetric ratio of oil to gas within the inclusion. Using commercial software (Aplin et al., 1999), these data along with inclusion homogenization temperature (Th) are used to reconstruct the bubble point for the inclusion oil and to obtain the pressure at the homogenization temperature, which is the minimum trapping pressure. The true trapping pressure can be obtained if coexisting aqueous inclusions are present in the sample by using the "crossing isochore technique" (Roedder, E., and Bodnar, R. J., 1980. Geologic Pressure Determination From Fluid Inclusion Studies. Ann. Rev. Earth. Planet. Sci. 8, 263–301).

One limitation of the confocal method is that the accuracy of the bubble point pressure calculation is heavily dependent on the initial oil composition entered by the user. Pressure-temperature "P-T" reports on nearby reservoired oils are presently the best data available to infer the P-T properties of oil inclusions. However, it is understood that inclusions trapped in the geological past may not be similar to present-day reservoired oil. Also, for many frontier locations these P-T reports are not available. An additional limitation of this method is that it can be used only for oil inclusions. This limits the application of the method mostly to the systems that contain oil. This method cannot be used for gas systems and for non-hydrocarbon systems. A method is needed for more robust and reliable pressure determination from fluid inclusions in sedimentary basins.

After an oil leg is penetrated during a drilling operation, there is the need to evaluate nearby gas resources. The conventional method of identifying gas cap from an oil leg involves down-hole sampling of reservoir oil and measuring its P-T properties. Reservoir fluid sampling is very expensive and new inexpensive methods, such as fluid inclusion based techniques, are needed for evaluating nearby gas accumulations.

Accordingly, a need exists for a reliable method for using fluid inclusions in rocks to reconstruct paleo-pressure history to evaluate hydrocarbon potential of sedimentary basins which overcomes the problems inherent in prior techniques. The present invention satisfies this need.

SUMMARY OF THE INVENTION

A method, based upon spectroscopy (e.g. Raman spectroscopy) and microthermometry of aqueous inclusions which are very common in sedimentary rocks, is described which results in more robust and reliable estimation of the paleo-pressure and paleo-salinity of fluids in sedimentary basins.

One embodiment is a method of determining pressure at the time of formation of fluid inclusions contained in sedimentary rocks. This method comprises; (a) identifying a fluid inclusion in a rock sample for analysis; (b) measuring the homogenization temperature of said fluid inclusion; (c) measuring the optical spectrum of methane and water in said fluid inclusion; (d) determining the relationship of homogenization temperature and optical spectrum to; formation pressure for said fluid inclusion; and (e) estimating formation pressure of said fluid inclusion from said relationship and said measurements of homogenization temperature and optical spectrum.

In another embodiment, the invention comprises (a) preparing samples to obtain both high quality images of the fluid phases in individual inclusions and optical spectra (i.e. ultraviolet, visible, infrared) of the fluid components with sufficient discrimination from fluorescence, Raman bands from non-inclusion material, and other interfering optical radiation; (b) determining the homogenization temperature at which the aqueous inclusion fluid components homogenize into a single fluid phase; (c) deter the relative methane composition of the inclusions from the spectra; (d) obtaining the salinity of the aqueous inclusions from the spectra; (e) using the methane concentration, salinity from aqueous inclusions and homogenization temperature from aqueous, oil and/or gas inclusions to estimate the physical conditions, such as pressure, and the geochemical environments in which the fluids were trapped; and (f) relating this information to the evaluation of sedimentary basins for their hydrocarbon potential and quality. Preferably, the spectra used to determine methane composition of the inclusions are obtained at homogenization temperature.

The invention is described with reference to aqueous fluid inclusions from core, cuttings, and outcrop samples, henceforth called rock fragments, obtained from petroleum environments. The inclusions of interest to the instant invention are formed in optically transparent minerals such as quartz, carbonate, feldspar, halite, fluorite or salt. For these inclusions, methane is the predominant, but not necessarily the only, hydrocarbon fluid and is generally a minor (approximately less than 10 percent weight, "wt. %") constituent in water. The water may contain 0 to 25 wt. % or more of NaCl or other salts. The inclusion fluids typically homogenize to a single phase at temperatures below 300° C.

The spectroscopy used for the method may be Raman spectroscopy, or any other suitable optical spectroscopy, in the ultraviolet, visible, or infrared portions of the electromagnetic spectrum. The only requirement is that vibrational bands of the methane and water in the individual inclusion can be determined and related to pressure.

Salinity may be measured by either of two novel methods involving spectroscopy. One method is the pattern recognition method, the other method is the chemometric method. Less preferably, salinity may be determined by conventional freezing point depression methods, which are known in the art.

The pressure obtained from fluid inclusions can be used to evaluate hydrocarbon potential of sedimentary basins. In particular, pressure from fluid inclusions can be applied to evaluate paleo and present-day pressure, timing of hydrocarbon migration, timing of seal failure and likelihood of a gas cap in a reservoir.

BRIEF DESCRIPTION OF THE DRAWINGS

The present invention and its advantages will be better understood by referring to the following detailed description and the attached drawings in which.

DETAILED DESCRIPTION OF THE PREFERRED EMBODIMENTS

In the following detailed description, the invention will be described in connection with its preferred embodiments. However, to the extent that the following description is specific to a particular embodiment or a particular use of the invention, this is intended to be illustrative only. Accordingly, the invention is not limited to the specific embodiments described below, but rather, the invention includes all alternatives, modifications, and equivalents falling within the true scope of the appended claims.

One preferred embodiment of the invention is the use of spectral analysis from laser-induced Raman scattering to determine both the methane concentration and salinity of the aqueous inclusion fluids and use this information to calculate the inclusion trapping pressure. Knowledge of the inclusion trapping pressure can be used for estimating (a) hydrocarbon migration timing; (b) paleo-pressure histories, or present reservoir pressures; and (c) timing and pressure conditions of seal failure.

Preparation of the sample to be analyzed involves consolidating the inclusion-bearing rock fragments with a medium consolidant or impregnant that has relatively low absorption and low fluorescence at photon energies corresponding to the Raman excitation and scattering by the fluid constituents. In addition, the consolidant should exhibit low Raman scattering cross-sections for species other than the inclusion constituents. The refractive index difference between the inclusion matrix and consolidant should be small to minimize optical scattering at their interfaces. Furthermore, the viscosity of the consolidant, before hardening, should be sufficiently low so that air bubbles can be easily removed. A preferred consolidant is EPO-FIX epoxy which is commercially available from Struers A/S, Valhojs Alle 176, DK-2610 Rodovre, Denmark. Preparation of the sample using this consolidant is disclosed below.

Thin sections are cut from the consolidated rock fragments and optically polished on both cut sides to permit high quality visualization through an optical microscope. The thin-section can be mounted on a suitable substrate to provide structural integrity during the polishing and subsequent handling for measurement.

The material (affixant) used to affix the thin-section to the substrate preferably has the same attributes as the consolidant and furthermore should not chemically react with the consolidant to produce reaction products that fluoresce or otherwise produce radiation that interferes with the fluid component's Raman spectrum. The consolidant and affixant are preferably stable to at least the homogenization temperature of the inclusion samples for a time sufficient to make the measurements. Preferably, the consolidant and affixant are the same material.

Figure 1:
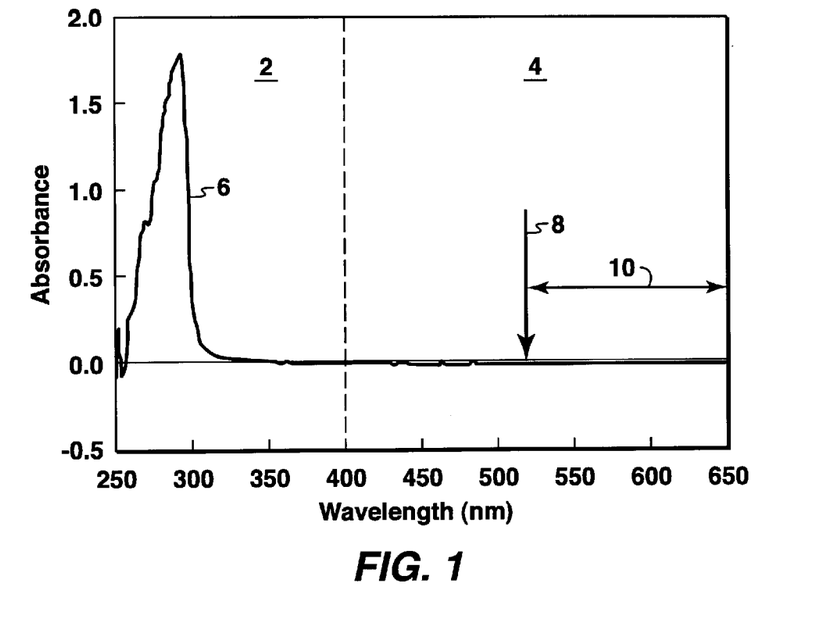
FIG. 1 illustrates UV and visible absorption spectrum of a preferred impregnant or consolidant used to consolidate the rock fragments so that a thin-section sample can be prepared for analysis.

FIG. 1 shows the ultraviolet and visible absorption spectrum of the EPO-FIX epoxy consolidant thin-section mounted on a microscope slide. The amount of light absorbed (absorption) when passing through material is expressed as absorbance. Absorbance is defined as the common logarithm of the ratio of the intensity of the light entering a sample to the light intensity leaving the sample. The absorbance of the glass slide is subtracted out of the total spectrum, so FIG. 1 shows just the absorbance of the consolidant material. In FIG. 1, the ultraviolet portion 2 of the spectrum is to the left of 400 nm while the visible portion 4 of the spectrum is to the right of 400 nm. Curve 6 represents absorbance and arrow 8 represents the laser excitation wavelength at 514 nm. FIG. 1 illustrates that there is negligible absorption by the consolidant in the visible portion 4 of the spectrum at the laser excitation wavelength and in the wavelength range 10 in which the Raman scattering from aqueous methane inclusions occur. Fluorescence is also negligible since there is no absorption.

The preferable fluid inclusions for analysis are those lying relatively close to the surface through which the laser excitation is introduced to minimize optical scattering loss of the incident laser light and Raman emission. In addition, minimizing the scattered light is important in that it can excite fluorescence in near-by petroleum species that may interfere with the lower intensity of Raman emission.

The preferred sample preparation technique is to use EPOXY EPO-FIX Resin, HQ manufactured by Struers. Struers part # EPOES is for the resin and Struers part # EPOHL is for the hardener. First, mix the EPOXY: 15 parts by volume of resin to 2 parts by volume hardener or 25 parts resin to 3 parts hardener by weight. Stir for at least 2 minutes. Prepare solid samples by cutting them to size suitable for an aluminum mold. The cuttings are cleaned with acetone, if necessary, and are then poured into the molds. After the samples are allowed to dry, the epoxy is mixed and poured into the molds.

The samples are allowed to cure overnight. After the samples are cured the aluminum molds are peeled off. The surfaces to be mounted are prepared for polishing. Polishing is done using 6 micron diamond paste followed by 3 micron diamond paste. The samples are then cleaned in a bath of isopropyl alcohol and mounted to a glass slide using the same epoxy.

Once the samples have cured, cut the excess away leaving 400 to 500 microns on the slide. The samples are ground to 150 microns in oil using a parallel thin section grinder. The samples are then lapped on a glass plate using kerosene and 600 grit silicon carbide to the desired thickness. Finally, the slides are placed back on the polishing machine and finished to a one micron diamond polished surface.

A Raman spectrum is obtained from the selected individual inclusion preferably at the homogenization temperature (i.e., the temperature at which the methane bubble and water homogenize to a single phase). The band area ratio of the symmetric stretching mode of dissolved methane and the broad stretching mode of liquid water is calculated from the spectra. A stretching mode is a fundamental vibration of the atoms that form a bond in a molecule where the bond length alternately elongates and compresses. In the symmetric stretching mode in methane ($CH_4$), the 4 hydrogen atoms simultaneously move away from, then toward, the central carbon atom. The frequency of this vibration in dissolved methane in water is about 2909 cm$^{-1}$. The stretching vibration for the oxygen-hydrogen (O—H) atoms in liquid water is broad in frequency ranging from 2900 to 3800 cm$^{-1}$.

The technique of confocal Raman microscopy is ideally suited to the small inclusion geometry. The laser radiation (514 nm Ar$^+$ laser) may be focused by the microscope objective to a diffraction-limited spot size which provides selected excitation of Raman scattering from the individual fluid phases within the inclusion. Discrimination against unwanted radiation from other parts of the sample is provided by the confocal optical system thereby enabling selective detection of the Raman scattering from a particular inclusion.

Small interferences from Raman scattering or fluorescence from the mineral matrix with the methane and water bands may be reduced by subtracting from the inclusion spectrum, a spectrum from a region of the sample that is adjacent to and at the same focal depth as the inclusion. All other conditions such as the laser power, integration time, and number of scans should be the same. Other techniques, that are known in the art (i.e., chemometric techniques), may be used to reduce the contribution of the matrix to the fluid inclusion's spectrum.

The methane content relative to the water may be determined from the band area ratio by calibration. Calibration of the band area ratio with methane concentration may be made using synthetic inclusions of known composition or an optical cell into which fluid constituents are introduced in known quantities. In the former case, the inclusions should be synthesized so as to preferably homogenize at temperatures below 300° C. and in the latter case, the cell should be operated isochorically (i.e., at a constant density), and pressure and temperature measurements should be made preferably at homogenization.

Figure 2:
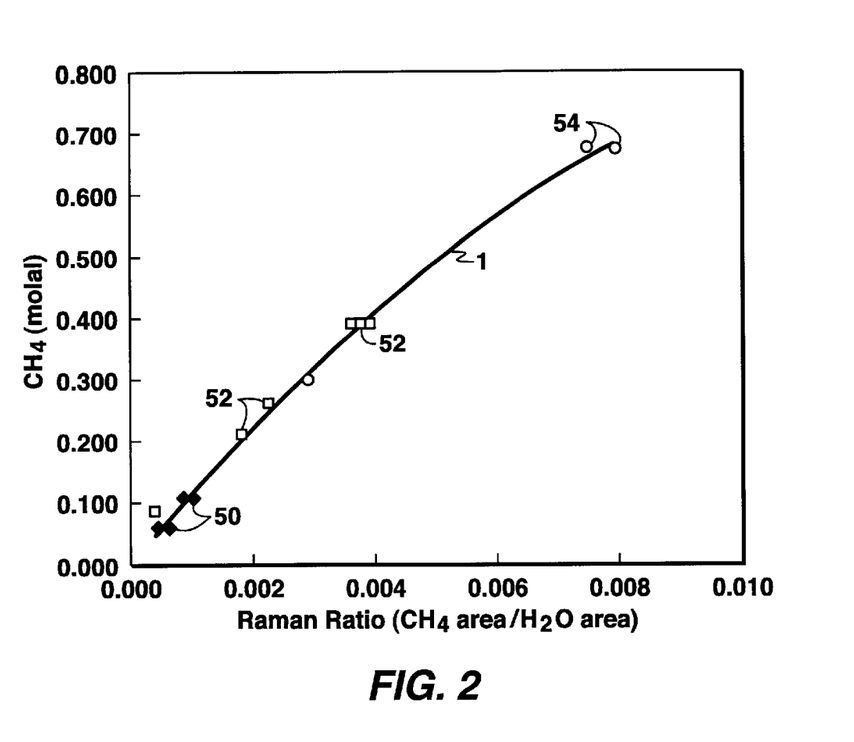
FIG. 2 illustrates calibration of methane concentration versus band area ratio of methane and water.

For fluid inclusions containing substantially only methane and brine (i.e. salt water), the ratio of the Raman band area for methane and water is related to the methane concentration. FIG. 2 illustrates calibration of methane concentration versus band area ratio of methane and water measured at the homogenization temperature. We have discovered that the band area ratio is substantially insensitive to both homogenization temperature and salinity and varies principally with the methane concentration. The initial model showed, unexpectedly, that while the band shapes change with composition and temperature, the band areas depend principally on the methane. Therefore, a feature of the present invention is the elimination of the costly calibration process of determining the Raman band ratio over wide ranges of temperature and salinity for each value of the methane content.

The band area ratios used for calibration may be formed from the as-measured spectra, or from post-measurement treated data. Examples of post-measurement treated data include but are not limited to corrections for polarization, temperature, and other detection and instrumental effects. However, the same protocol should be followed for each of the calibration samples and for subsequent analysis of unknown samples using the calibration thus obtained.

The band area ratio is plotted against the known methane to water concentration ratio to obtain a calibration curve. The calibration curve, shown in FIG. 2, obtained from synthetic inclusions, shows that the methane concentration in molality, Y, is related to the Raman band area ratio, X, of methane to water as in equation (1).

$$Y=-4255.8X^2+119.64X. \qquad (1)$$

Figure 3:
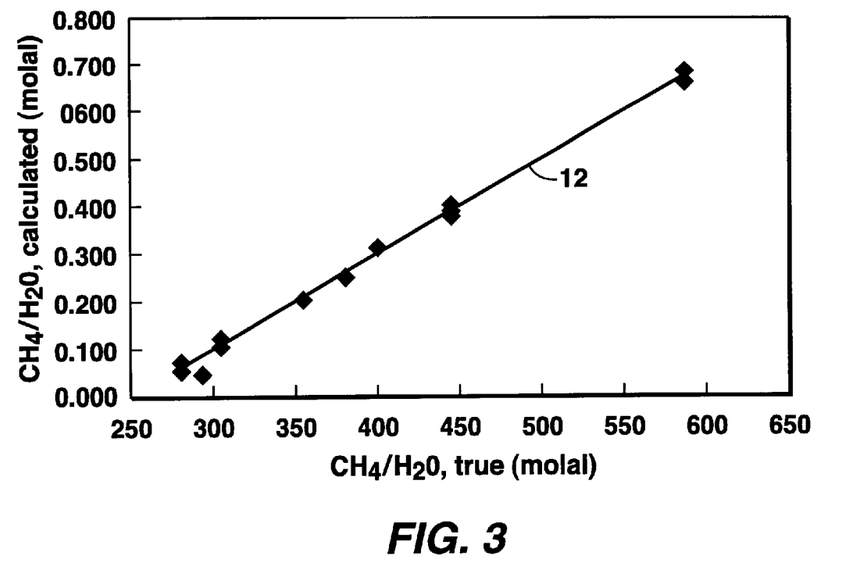
FIG. 3 shows a parity plot of the known methane concentration versus the calculated concentration using the calibration curve of FIG. 2.

The constants and functional dependence may vary with instrument and measurement and data reduction protocol. FIG. 3 is a parity plot showing the known (true) methane content versus that calculated from the Raman ratio and the quadratic regression equation (1) above. The standard error of calibration is 0.014 molal.

The data in FIG. 2, are for inclusions with salinities and homogenization temperatures of 0 wt. % percent and 110, 104, 98, 150, 118, 118° C., respectively 50; 10 wt. % percent 123, 110, 135, 154, 154, 155, 150, 155° C., respectively 52; and 25 wt. % percent 160, 280, 250° C., respectively 54 are plotted to illustrate the Raman band area ratio is insensitive to salinity and temperature. Four of the data points are overlapped in FIGS. 2 and 3.

While the salinity is not required to obtain the methane content, it is required, however, to determine the bubble-point for the fluid inclusion from an equation of state. We discovered that the salinity from fluid inclusions may be conveniently determined from the Raman water band obtained from the liquid water with dissolved salt phase at room temperature by at least two different methods. The two methods are the pattern recognition method and the chemometric method. Less preferably, salinity can be measured by conventional freezing point depression methods. However, the conventional method produces unreliable results for relatively small (less than 5 microns) inclusions that are typical for sedimentary environments.

Figure 4:
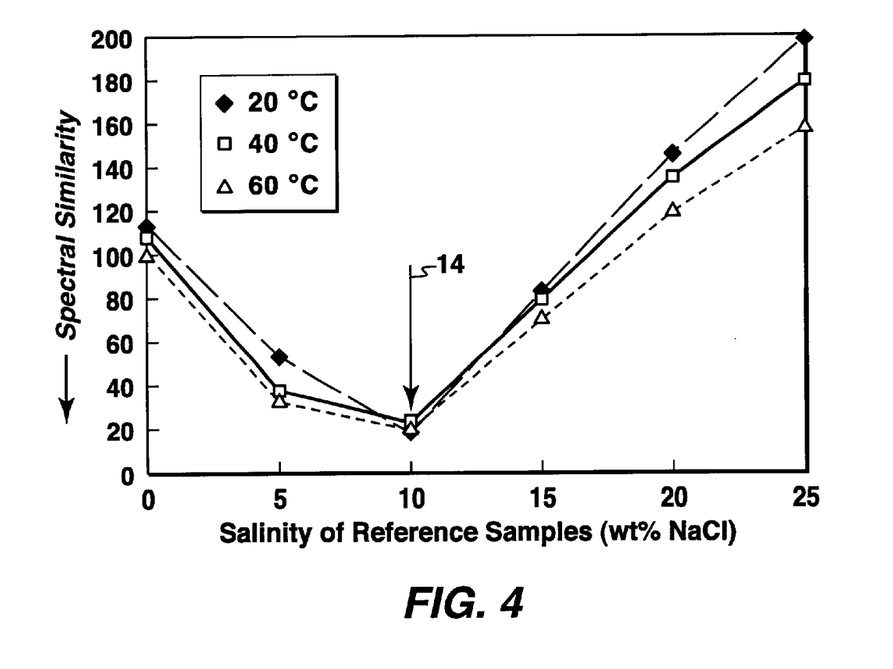
FIG. 4 illustrates predicted salinity from the pattern recognition method.

Estimating salinity by the pattern recognition method involves obtaining a calibration set of spectra from samples of known salinity. The spectrum of an inclusion whose salinity is unknown is collected at the same temperature and at similar experimental conditions as the salinity calibration spectra. FIG. 4 illustrates predicted salinity from the pattern recognition method. The spectra of the calibration and unknown samples are processed in the same way, so as to reduce the variability in the spectra that is due to factors other than variability in the salinity.

The pattern recognition method is applied pair-wise to the unknown and each of the calibration spectra, and produces a single number, Spectral Similarity, which is a measure of the similarity in shape between the two spectra. The smaller the Spectral Similarity value, the greater their spectral similarity. The underlying assumption of the method is that samples having the same shaped spectra have the same salinity. Thus, in FIG. 4, the salinity of the "unknown" sample (having 8 wt. % NaCl) is closest to the salinity of the calibration sample to which its spectral shape is most similar 14 (i.e, 10 wt. % NaCl). Alternatively, a regression model relating the Spectral Similarity parameter to the known salinity values of the calibration samples may be developed and used to predict the salinity of an unknown sample. A model developed using the spectra obtained for FIG. 4 predicts the "unknown" (8 wt. % NaCl) sample to have a salinity of 8.9 wt. %.

There are advantages of this method that are particularly important to Raman spectroscopy applied to fluid inclusions. Changes in the overall intensity, such as those caused by laser power variation, changes in focus or collection efficiency of the detection system, or changes in the optical path through the inclusion do not affect the predicted salinity values.

Calibration spectra for the pattern recognition method may be obtained from water samples contained in synthetic inclusions or in an optical cell. The temperature of the samples may range, practically, from above hydrate formation to homogenization to a single fluid phase but should be held constant during measurement. Operation at 20° C. is both convenient and preferable since it minimizes thermal gradients in the cell that may degrade the quality of the spectra. The calibration samples should span the salinity range of interest and the number of samples should be determined by the accuracy and resolution required by the application for which the data will be used.

The smallest difference in salinity between samples that can be determined by the method depends, in part, upon the repeatability of the spectra obtained on the calibration samples. Repeat measurements should be made for each value of the salinity including the preparation of a new solution for each measurement. Repeat measurements are required to determine the base case variability in the spectra when the chemical composition of the sample is unchanged; that is, where only instrumental factors and noise contribute to the variability. If the spectra of two chemically different samples differ by an amount less than the variability of repeat measurements made on a single sample, then the chemical differences cannot be differentiated. In other words, the variability in the repeat measurements represent the smallest compositional difference that can be determined by the method. Post-measurement processing of the data should include eliminating to the greatest extent possible variability in the spectra that are not due to changes in the salinity.

Similarly to the pattern recognition method, the chemometric method involves obtaining a set of spectra from samples of known salinity. The spectrum of a fluid inclusion whose salinity is unknown is collected at the same temperature and at similar experimental conditions as the calibration spectra. The spectra of the calibration and unknown samples are processed in the same way, so as to reduce the variability in the spectra that is due to factors other than variability in the salinity.

Figure 5:
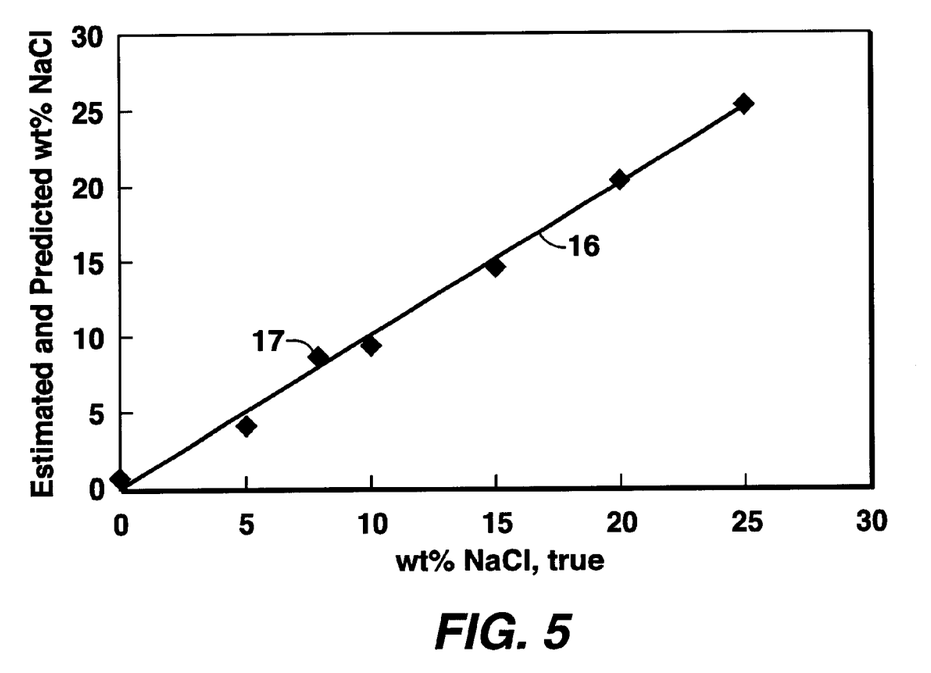
FIG. 5 illustrates predicted salinity from the chemometric method.

FIG. 5 illustrates a parity line 16 of the predicted salinity of the "unknown" (8 wt. % NaCl) sample 17 and the estimated calibration values using the chemometric method. The estimated calibration values result from a principal component regression model developed from the processed spectra and known values of the salinity. The regression model is then used to predict the unknown sample 17. The predicted value is 8.6 wt. % NaCl. Improvement in the prediction quality can be obtained by using additional calibration samples and post-processing of the spectra to remove instrumental effects (e.g. baseline).

Raman spectra have been used to determine salinity in fluid inclusions that do not contain measurable dissolved methane. This determination involves a more complicated method in which various parts of the water band are used to define a "skewing parameter" that is related to the salinity (Mernagh, T. P. and Wilde, A. R. Geochimica et Cosmochimica Acta, 53, 765–771 (1989)). The "skewing parameter" is a term that characterizes shape changes to the Raman water band for different amounts of salt (i.e. salinity) and for different temperatures. It depends on the ratio of the intensities at two specific spectral frequencies and a complicated function of specifically defined regions of the band. The methods we employ are not dependent upon any prescribed functional form of the water band. There is no indication, in the prior art as to the effect of dissolved methane on the "skewing parameter".

Figure 6:
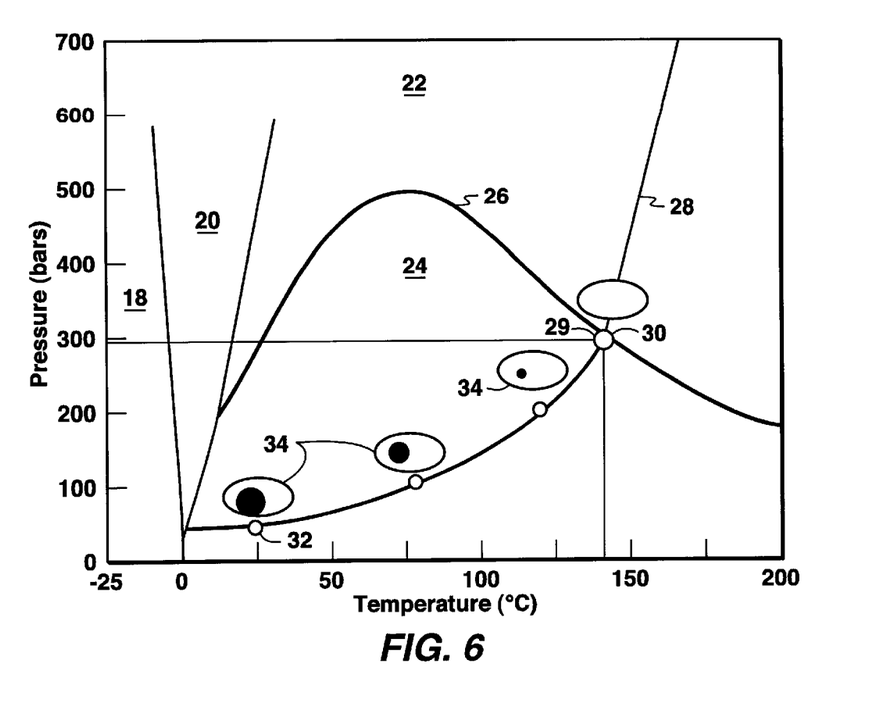
FIG. 6 illustrates a pressure-temperature (P-T) plot of the phase diagram for a water-methane system.

The inventive method can be used to calculate the inclusion bubble point pressure and fluid density. FIG. 6 is a pressure-temperature (P-T) plot of the phase diagram for an $H_2O$—$CH_4$ system. As an inclusion cools (after entrapment) from homogenization temperature 30 to room temperature 32 or lower, its internal pressure is determined by the P-T properties of fluid trapped within this inclusion at constant density and follows a path known as an isochore 28, The isochore represents the relationship between the pressure and temperature at constant density. When the internal pressure has dropped to the point where the isochore intersects the two-phase curve (bubble point curve or bubble point line 26) at homogenization temperature, a gas bubble nucleates 34 and continues to grow on further cooling.

The pressure at which the first gas bubble is formed is-the saturation or bubble-point pressure 29. Above the bubble point pressure 29 or bubble point line 26, the fluid contains a single liquid phase 22. At room temperature, the inclusion contains two phases—liquid and gas bubble 24. Below room temperature, the fluid inclusion contains hydrates (i.e., hydrate and liquid 20 and hydrate and ice 18). The natural cooling process can be reversed on the heating microscope stage. During heating, the bubble will decrease in size and disappear at homogenization temperature (i.e., when the inclusion will reach the bubble point pressure 29). The inclusion bubble point pressure 29 and fluid density for FIG. 6 are obtained from equations of state for the properties of homogenization temperature, the methane concentration, and salinity derived from the Raman spectrum for a specific inclusion. For any aqueous inclusion that is saturated with gas, the estimated bubble pressure at the homogenization temperature represents the true trapping pressure and true temperature respectively.

We have discovered that gas-saturated aqueous inclusions are common for hydrocarbon accumulations with a free gas cap (gas reservoirs and oil plus gas reservoirs). For these reservoirs, gas-saturated aqueous inclusions can be recognized by their petrographic relationship with gas inclusions. If aqueous inclusions coexist (i.e., trapped at the same time) with gas inclusions, than these aqueous inclusions are saturated with gas. This technique assumes water and gas are in equilibrium. For oil plus gas reservoirs, gas-saturated aqueous inclusions can be recognized by comparing their homogenization temperatures to the homogenization temperatures of coexisting oil inclusions. Both the aqueous and oil inclusions must exhibit equal homogenization temperatures. The technique assumes water, oil and gas are in equilibrium.

For aqueous fluid inclusions undersaturated with gas, the pressure at the homogenization temperature is the minimum trapping pressure. These inclusions are typical in undersaturated oil reservoirs without free gas caps. Under these conditions, aqueous inclusions show higher homogenization temperatures than the homogenization temperatures of coexisting oil inclusions.

Different generations of fluid inclusions can be discriminated based on petrographic examination of the rock thin-section. Using this inventive method bubble point pressure can be measured from different generations of aqueous inclusion that were trapped in the rock over its diagenetic history up to the present time. Therefore, the present invention provides the ability to reconstruct paleo-pressure history of the rock sample.

The present invention may be used to develop accurate models of the relationship of homogenization temperature and optical spectrum to formation pressure. Data from the present invention may be used to develop the models using modeling techniques known in the art (i.e., the chemometric method and the pattern recognition method discussed previously). It is believed that there is a universal relationship of homogenization temperate and optical spectra to formation pressure. Therefore, these models will permit estimation of the inclusion formation pressure directly from homogenization temperature and optical spectra of fluid inclusions.

Determining the relationship of homogenization temperature and optical spectrum to formation pressure, as discussed above, is necessary for one embodiment. This embodiment is a method of determining pressure at the time of formation of fluid inclusions contained in sedimentary rocks. The method comprises the steps of first, identifying a fluid inclusion in a rock sample for analysis. The second step is measuring the homogenization temperature of said fluid inclusion and the third step is measuring the optical spectrum of methane and water in said fluid inclusion. The fourth step is determining the relationship of homogenization temperature and optical spectrum to formation pressure for said fluid inclusion. The fifth and final step is estimating formation pressure of said fluid inclusion from said relationship and said measurements of homogenization temperature and optical spectrum.

Additional work will develop the present invention into a more accurate, reliable and relatively rapid technique for explorationists to routinely characterize fluid inclusions encountered in sedimentary environments. Towards this end, calibration over the composition, pressure, and temperature range of interest in sedimentary environments. In addition, other factors affecting the accuracy of the method, when applied broadly to geological samples, may be identified and a measurement protocol may be developed.

The paleo-pressure from individual aqueous fluid inclusions can be used for analyzing (a) hydrocarbon migration timing; (b) paleo-fluid flow, paleo-pressure histories, or present reservoir pressures; and (c) timing and pressure conditions of seal quality and failure. In basin modeling, these parameters are usually very poorly constrained.

The pressures that subsurface beds experience through the burial process are difficult to calculate and are a major source of uncertainty. Typically, broad ranges of pressures through time are assigned to the beds related to the estimated column of overlying rock, speed of burial, and surrounding rock properties as the bed is buried. Based on this information, paleo-history of the beds are constructed by modeling. Our methods use aqueous fluid inclusions, that are very common in sedimentary rocks, to directly measure pressures experienced by the rock during its burial history. More specifically, this method uses bubble-point pressure measurements from aqueous inclusions saturated with gas.

Each aqueous fluid inclusion in mineral cements has a unique bubble point, or saturation pressure. For aqueous inclusions saturated with gas, this pressure corresponds to the true trapping pressure. The inventive method can determine trapping pressures and temperatures from different generations of gas-saturated aqueous inclusions that were trapped in the rock over its diagenetic history. This permits reconstruction of paleopressure history of the rock sample.

The invention provides the ability to (a) obtain trapping pressure and temperature for the inclusions (inclusion trapping conditions); (b) plot the inclusion trapping conditions on a pressure versus temperature diagram to reconstruct pressure-temperature history of the bed; (c) if burial history is available from basin modeling, plot the burial history of the bed of interest on a pressure versus temperature diagram through time along with the inclusion trapping conditions; and (d) compare the fluid inclusion data with modeled burial history data. The inclusion trapping P-T conditions should lie on the burial history curve. If not, the burial history data should be adjusted accordingly.

Fluid inclusions can be used to obtain down-hole pressure at present-day conditions. This application is especially important for high temperature-high pressure reservoirs where conventional tools can not be easily applied. The procedure of obtaining present-day pressure from fluid inclusions includes the steps of (a) measuring homogenization temperature for aqueous inclusions from different fluid inclusion generations; (b) comparing the homogenization temperatures with temperature measured at the same depth as the rock samples from which fluid inclusions are observed (present-day temperature), if inclusion homogenization temperature is equal to the present-day temperature, then the inclusion was trapped at present-day conditions; and (c) obtaining trapping pressure for these inclusions using the present invention.

Knowledge of the timing of hydrocarbon migration is critical for exploration for oil and gas. It can be used to estimate the time at which hydrocarbons were trapped as fluid inclusions in cement and correlate the timing of hydrocarbon migration to the timing of diagenetic cement precipitation for reservoir quality or fracture studies. This application utilizes bubble-point pressure measurements from coexisting aqueous and hydrocarbon fluid inclusions combined with a burial history curve for the bed from which the fluid inclusion samples are analyzed.

Each fluid trapped within inclusions in mineral cements has unique bubble point, or saturation pressure. For aqueous inclusions saturated with gas, the point at which this bubble point curve crosses the burial-history curve when both are plotted on a pressure-temperature chart, should correspond to the age of entrapment for that inclusion. For aqueous inclusions undersaturated with gas, a unique line of equal density, or isochore, can be drawn extending upward from the bubble-point curve at the homogenization temperature. The point at which the isochore crosses the burial-history curve, should correspond to the inclusion age.

Figure 7:
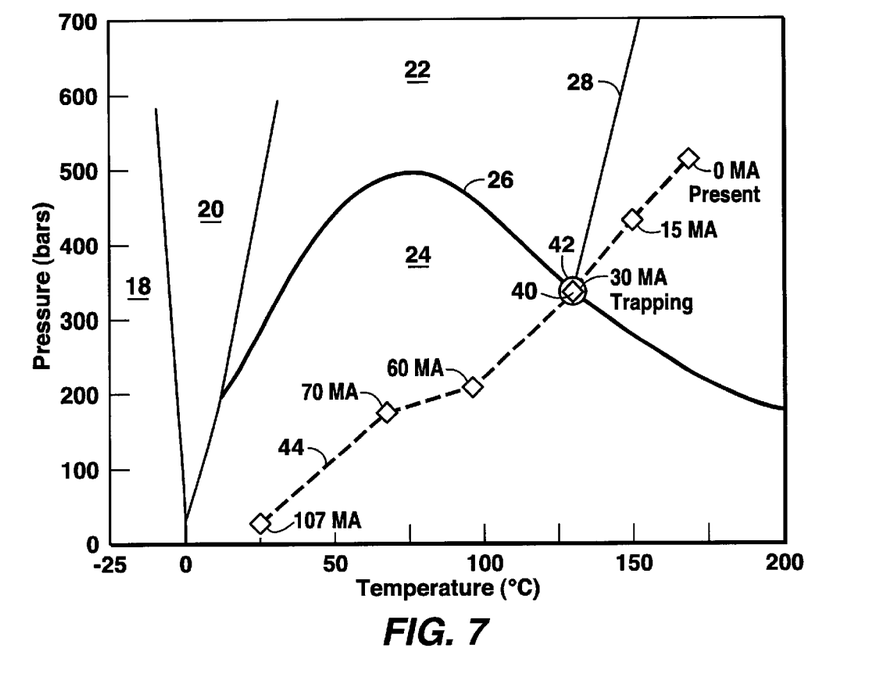
FIG. 7 illustrates a burial history curve on a pressure-temperature plot.

There are several steps for estimating migration timing from coexisting oil and aqueous fluid inclusion assemblages. First, as illustrated in FIG. 7, plot the burial history 44 of the bed of interest on a pressure versus temperature diagram. These plots are typically made using basin modeling software. Using transmitted and ultraviolet fluorescence microscopy, locate oil and aqueous inclusions that represent immiscible inclusion pairs trapped at the same time. Immiscible inclusion pairs trapped at the same time are the inclusions that are trapped from an immiscible fluid (i.e., water and petroleum). Contemporaneous entrapment of oil and water inclusions is recognized based on textural criteria. The best indicator of contemporaneous inclusion entrapment is when the inclusions occur in the same micro-fracture or growth zone. Obtain bubble-point curves 26 for aqueous inclusions from each inclusion pair. Plot the bubble-point curve 26 and isochore 28 for these inclusions along with a burial history curve 44.

For aqueous inclusions saturated with gas, the point 42 at which the bubble point curve crosses the burial-history curve, when both are plotted on a pressure-temperature chart, should correspond to the age of entrapment for that inclusion. Trapping pressure and temperature are obtained from the inclusion bubble-point curve. These conditions should occur at the intersection of the inclusion bubble-point curve and the burial history curve 42. If not, the burial history curve should be adjusted to intersect the inclusion trapping conditions. For aqueous inclusions, undersaturated with gas, the point at which the inclusion isochore crosses the burial-history curve, corresponds to the inclusion age 40. The fact that the intersection of the bubble point curve and history curve 42 is the same point as the intersection of the inclusion isochore and burial history curve 40 in FIG. 7 is purely coincidental and the two points will not necessarily be the same.

Knowledge of the pressures exerted on reservoir and seal beds through time as they are buried is important in hydrocarbon exploration. If the pressures exerted on a prospective seal bed are sufficiently high to rupture the seal or cause the seal to leak, then the underlying hydrocarbons will migrate and not be trapped at a prospect location. If seal failure has occurred, it may be important to determine the geologic time of the failure for migration analysis, further prospecting in the area, and general hydrocarbon systems analysis.

Standard industry practice is to use burial history models that calculate the time-temperature evolution of beds as they are buried in the subsurface. The pressures that subsurface beds experience through the burial process are difficult to calculate and are a major source of uncertainty. Typically, broad ranges of pressures through time are assigned to the beds related to the estimated column of overlying rock, speed of burial, and surrounding rock properties as the bed is buried. If seal failure has occurred and samples of the reservoir rock below or adjacent to the seal are available through drilling, the present invention can be used along with the burial history models to estimate seal failure timing.

There are several steps for estimating seal-failure timing from aqueous inclusions. Suitable aqueous inclusions, using the "inclusion gas saturation" criteria are selected for estimation of true trapping pressure. Using this invention, trapping pressure and temperature are obtained from selected inclusions (inclusion trapping conditions). Homogenization temperature is used to estimate the temperature of the bed at the time the inclusion was formed. The time of inclusion formation is obtained from time-temperature burial history models. In FIG. 7, the inclusion pressure is combined with the time-temperature-pressure history curve 44. Pressure history is then compared to estimated leak-off pressures of the seal through time to determine possible time and pressure related to seal failure.

Aqueous and oil inclusions can also be used in predicting gas resources. We have discovered that coexisting aqueous and oil inclusions can be used to evaluate whether a gas cap exists updip from an oil penetration. For example, if coexisting oil and water inclusions with equal homogenization temperatures are detected in an oil leg, and homogenization temperature is substantially equal to the present-day reservoir temperature, then it is very likely that a gas cap is present updip from the oil leg. In an oil-water-gas system, oil and water equilibrate with the gas cap and become saturated with gas. As equilibrium is approached, the homogenization temperatures of both oil and aqueous inclusions will converge. At saturation, both the oil and aqueous inclusions will be at their bubble points and their homogenization temperatures will be identical.

If the homogenization temperature of an oil inclusion is substantially equal to the homogenization temperature of an aqueous inclusion, and homogenization temperature is not substantially equal to the present-day reservoir temperature, then a paleo-gas cap was likely at the homogenization temperature. A paleo-gas cap or ancient gas cap is likely at homogenization temperature because gas-saturated aqueous inclusions are common for hydrocarbon accumulations with a free gas cap. If the homogenization temperature of an oil inclusion is substantially less than the homogenization temperature of an aqueous inclusion, then the oil leg is undersaturated with gas, and a gas cap is unlikely at time of inclusion entrapment.

EXAMPLES

An inclusion-bearing cuttings sample was taken from a formation known to contain hydrocarbons. The procedure for calculating trapping pressure for these samples includes the following steps illustrated in the graphical flow chart of FIG. 8.

Figure 8:
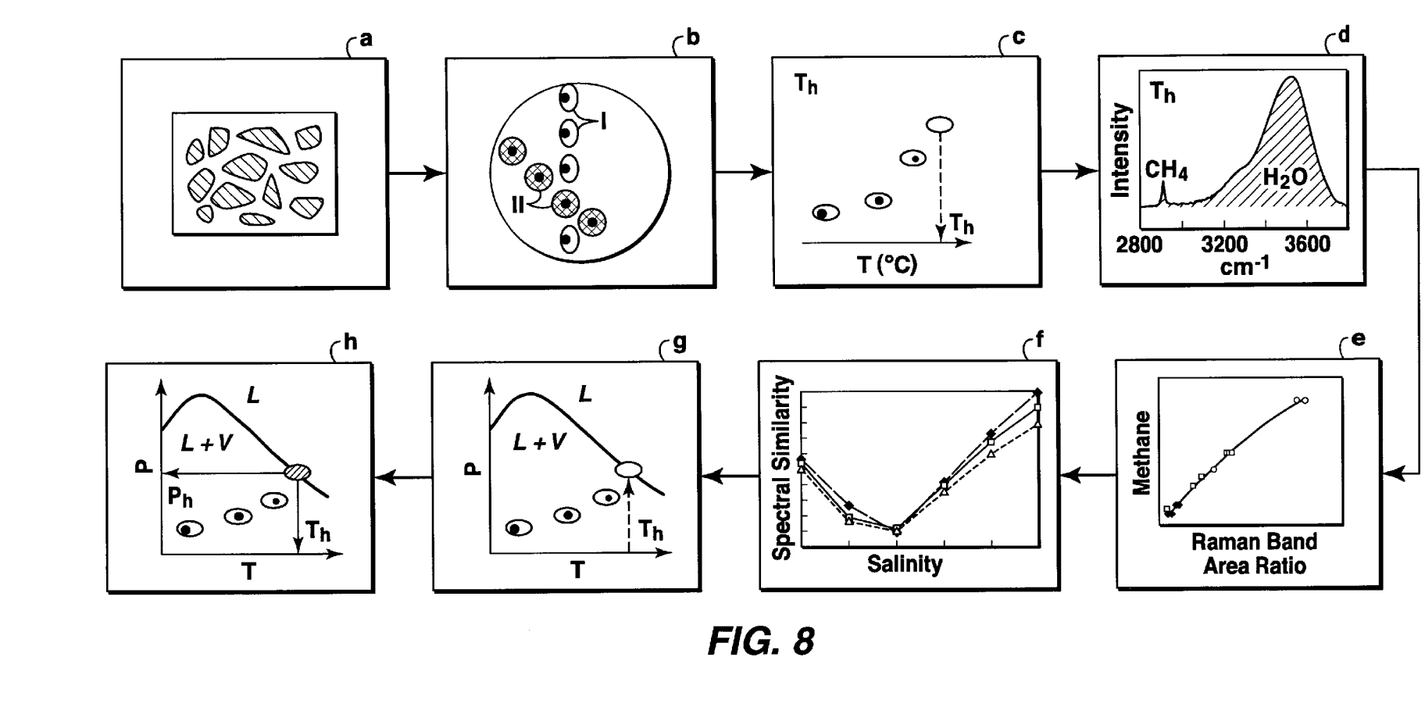
FIGS. 8 is a graphical flow chart of a pressure estimation procedure from fluid inclusions.

First, step a requires consolidating the cutting sample with the consolidant, cutting a thin section from the consolidated rock fragments, polishing the thin section on both cut sides to permit high quality visualization through an optical microscope.

In step b the cuttings sample is examined under the petrographic microscope to determine whether more than one population of fluid inclusions are present. For example, in FIG. 8 two different populations of coexisting aqueous and oil inclusions were identified: population I and population 11. The relative dates of the fluid inclusion populations are determined by fluid inclusion petrographic techniques which are known in the art. Coexisting aqueous and oil inclusions from both populations I and II showed identical homogenization temperatures measured using the conventional heating method. These homogenization temperature values indicate that the inclusions are saturated with gas. Inclusion population II showed a homogenization temperature similar to the down-hole temperature at this depth, suggesting that this inclusion population was trapped at the present-day temperature and pressure. Inclusion population I gave a homogenization temperature of 105° C., which is lower than the present-day temperature. Basin modeling data indicate that the stratigraphic unit in which population I resides reached temperature of 105° C. 2 million years ago "Ma". This 2 Ma is the time at which this population was trapped.

Step c involves collecting Raman measurements on individual inclusions from each inclusion generation at the homogenization temperature (at which the vapor and liquid inclusion phases homogenize to a single phase). Inclusion homogenization temperatures are measured using a conventional heating-freezing stage.

During step d the band area ratio of the symmetric stretching mode of dissolved methane and the O—H stretching mode of water are calculated from the Raman spectra obtained from the inclusions.

Step e is a determination of the methane concentration from the Raman band area using previous calibration (calibration using synthetic inclusions of known composition and/or an optical cell into which fluid constituents are introduced in known quantities). According to our invention, the methane content can be determined without prior knowledge of inclusion salinity or homogenization temperature.

In step f salinity is required to determine the bubble-point of the inclusion composition. Salinity is estimated from Raman spectra using either the pattern recognition method (as illustrated in FIG. 8f) or the chemometric method (not illustrated). Less preferably, salinity can be measured by conventional freezing point depression methods.

Step g uses the equations of state for the $H_2O$—NaCl—$CH_4$ system to calculate the bubble-point for the inclusions. The input data for this calculation are the inclusion salinity and methane content (both obtained from Raman spectra) and the homogenization temperature.

Finally, in step h the bubble point pressure for the inclusion is estimated at the homogenization temperature. For the inclusions studied (saturated with gas), both the bubble-point pressures and trapping pressure should be equal. The pressure obtained for the inclusion population 11, which was trapped at the present-day conditions, is within 10% error of measured present-day pressure.

The foregoing description has been directed to particular embodiments of the invention for the purpose of illustrating the invention. It will be apparent to persons skilled in the art, however, that many alternatives, modifications, and variations to the embodiments described herein are possible. All such alternatives, modifications, and variations are intended to be within the scope of the present invention, as defined by the appended claims.

We claim:

1. A method of determining pressure at the time of formation of fluid inclusions contained in sedimentary rocks comprising the steps of:

identifying a fluid inclusion in a rock sample for analysis;

measuring the homogenization temperature of said fluid inclusion;

measuring the optical spectrum of methane and water in said fluid inclusion;

determining the relationship of homogenization temperature and optical spectrum to formation pressure for said fluid inclusion; and estimating formation pressure of said fluid inclusion from said relationship and said measurements of homogenization temperature and optical spectrum.

2. The method of claim 1 wherein said optical spectrum is obtained from the group of spectral analyses consisting of infrared, ultraviolet, visible spectral analysis and any combination thereof.

3. The method of claim 1 wherein formation pressure of at least one fluid inclusion is used to evaluate a sedimentary basin for likelihood of hydrocarbons.

4. The method of claim 1 wherein said fluid inclusions are selected from the group consisting of aqueous fluid inclusions containing methane and salt, aqueous fluid inclusions coexisting with oil fluid inclusions, aqueous fluid inclusions coexisting with gas fluid inclusions, aqueous inclusions without coexisting hydrocarbon inclusions, and any combination thereof.

5. A method of determining pressure at the time of formation of fluid inclusion contained in sedimentary rocks comprising the steps of:

preparing a sample for examination;

identifying a fluid inclusion for temperature and pressure measurements;

measuring said fluid inclusion's homogenization temperature by heating said sample until inclusion fluids homogenize;

measuring said fluid inclusion's optical spectrum;

determining band area ratios of dissolved methane and water from optical spectra obtained from calibration samples of known composition, including methane concentration and known homogenization temperatures;

determining band area ratio of dissolved methane and water from said fluid inclusion's optical spectrum;

determining a methane concentration for said fluid inclusions by comparing said band area ratio of said inclusion to said band area ratio of calibration samples;

determining salinity of said fluid inclusion sample;

determining saturation pressure for said fluid inclusion from the fluid inclusion homogenization temperature, salinity, and methane concentration; and determining whether said saturation pressure is equal to minimum trapping pressure or true trapping pressure.

6. The method of claim 5 wherein Raman spectroscopy is used to obtain said fluid inclusion optical spectrum.

7. The method of claim 5 wherein said spectrum of methane and water is obtained from said fluid inclusion substantially at homogenization temperature of said fluid inclusion.

8. The method of claim 6 wherein said sample is prepared by using a consolidant that is chosen so that when cured it exhibits the properties of low-absorbing and low-fluorescent in the spectral range corresponding to the Raman excitation and scattering by the inclusion fluid constituents, weak Raman scattering, has a small difference in refractive index compared with the inclusion matrix to minimize optical scattering at the interfaces, before curing has a viscosity that is sufficiently low that bubbles can be easily removed.

9. The method of claim 8 wherein the sample is attached to a substrate by using an affixant.

10. The method of claim 6 wherein interference from Raman scattering or fluorescence from the mineral matrix with the methane and water bands are reduced by subtracting from the inclusion spectrum, a spectrum from a region of the sample that is adjacent to and at the same focal depth as said fluid inclusion.

11. The method of claim 5 wherein chemometric techniques are utilized to reduce the contribution of the matrix to said fluid inclusion spectrum.

12. The method of claim 5, wherein the salinity of said fluid inclusion is determined by comparing said fluid inclusion spectrum, determining the greatest similarity between inclusion spectrum and one or more of the spectra of known salinity and salt type and selecting said salinity and salt type as being substantially the same salinity as known sample having the most similar spectra to said fluid inclusion sample.

13. The method of claim 5 where said salinity is determined by developing at least one model from said spectra of known salinity to predict the salinity of unknown sample and comparing spectra of samples of known salinity to spectrum of the inclusion sample with unknown salinity.

14. The method of claim 5 wherein an equation of state for water-salt-methane is obtained and homogenization temperature of said fluid inclusion is used to determine the pressure at homogenization from said equation of state for water-salt-methane.

15. The method of claim 5 wherein relative dates of the fluid inclusions in the rock are determined by fluid inclusion petrographical techniques.

16. The method of claim 5 wherein pressure and relative dates of fluid inclusion formation are used to reconstruct burial history of the rock sample.

17. The method of claim 5 wherein pressure and temperature of fluid inclusions is used to determine hydrocarbon migration timing.

18. The method of claim 5 wherein pressure and temperature of fluid inclusion formation are used for timing and pressure conditions of seal failure.

19. The method of claim 5 wherein likelihood of gas reservoirs is predicted by comparing homogenization temperature of oil inclusions and aqueous inclusions.

20. The method of claim 5 wherein true present-day formation pressure is determined by:

measuring homogenization temperature of said fluid inclusion from a geological sample at some depth;

comparing homogenization to present-day temperature at this depth; and determining if pressure obtained from said fluid inclusion indicates true present-day formation pressure.

21. The method of claim 5 wherein pressure and temperature obtained from coexisting gas and aqueous inclusions are estimated to be true trapping pressure and temperature.

22. The method of claim 5 wherein true fluid inclusion formation temperature and pressure for coexisting oil and aqueous inclusions are estimated by measuring homogenization temperature of an oil inclusion and homogenization temperature of a coexisting aqueous inclusion and determining homogenization temperature and saturation pressure to represent true formation temperature and pressure for said fluid inclusions if the coexisting oil and aqueous inclusions exhibit equal homogenization temperature.

23. The method of claim 5 wherein likelihood of finding a gas reservoir is evaluated by finding coexisting oil and aqueous inclusions in rock samples from an oil leg and determining the likelihood of a gas cap by comparing the homogenization temperatures of coexisting oil and aqueous inclusions.

24. The method of claim 5 wherein paleo-pressure history of the rock is determined by plotting inclusion trapping conditions on a pressure versus temperature diagram to reconstruct pressure and temperature history of the bed.

25. The method of claim 5 wherein paleo-pressure history of the rock, is determined by:
    plotting burial history of said bed on a pressure versus temperature diagram through time along with said fluid inclusion trapping conditions;
    comparing said fluid inclusion data with modeled burial history data; and
    adjusting burial history data, as needed if said pressure temperature conditions do not lie on history curve.

26. The method of claim 5 wherein present-day pressure is estimated by:
    measuring homogenization temperature for aqueous inclusions from different fluid inclusion generations;
    comparing homogenization temperatures with temperature at depth of said sample with said fluid inclusions; and
    determining pressure of formation to be substantially equal to present day formation pressure if said fluid inclusion homogenization temperatures are equal to present day temperature at depth of said sample.

27. The method of claim 5 wherein hydrocarbon migration timing is estimated by:
    plotting burial history of a bed of interest on a pressure versus temperature diagram through time;
    locating oil and aqueous inclusion pairs that were trapped at the same time;
    adjusting the modeled burial history curve to fit the measured pressure and temperature data; and
    estimating the time of inclusion entrapment.

28. The method of claim 27 wherein the measured pressure and temperature data are used to estimate the time at which hydrocarbons were trapped as fluid inclusions in cement by correlating the timing of hydrocarbon migration to the timing of diagentic cement precipitation for these inclusions.

29. The method of claim 5 wherein seal failure timing is determined by the following steps:
    selecting inclusions suitable for estimation of true trapping pressure;
    obtaining trapping pressure and temperature from said selected inclusions;
    combining inclusion pressure with time-pressure history of bed;
    comparing pressure history to estimate leak-off pressures of seal to determine possible time and pressure related to seal failure.

30. A method of determining pressure at the time of formation of fluid inclusions contained in sedimentary rocks comprising the steps of:
    identifying a fluid inclusion in a rock sample for analysis;
    measuring the homogenization temperature of said fluid inclusion;
    measuring optical spectra of methane and water in said fluid inclusion;
    determining the relationship of homogenization temperature and optical spectra to formation pressure for said fluid inclusion; and
    estimating formation pressure of said fluid inclusion from said relationship and said measurements of homogenization temperature and optical spectra.

* * * * *